United States Patent
Toyoshima et al.

(10) Patent No.: US 6,888,046 B2
(45) Date of Patent: May 3, 2005

(54) TOPSHEET FOR ABSORBENT ARTICLE

(75) Inventors: Yasuo Toyoshima, Hochigi (JP);
Noriko Sakamoto, Tochigi (JP);
Hiroko Sugiura, Tochigi (JP);
Takanobu Miyamoto, Tochigi (JP);
Wataru Saka, Tochigi (JP); Shoichi Taneichi, Tochigi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/360,619

(22) Filed: Feb. 10, 2003

(65) Prior Publication Data

US 2003/0167044 A1 Sep. 4, 2003

(30) Foreign Application Priority Data

Feb. 25, 2002 (JP) ........................................ 2002-047354
Mar. 22, 2002 (JP) ........................................ 2002-082173

(51) Int. Cl.[7] .............................................. A61F 13/15
(52) U.S. Cl. ................ 604/380; 604/378; 604/385.101; 604/383
(58) Field of Search ................................. 604/378, 380, 604/383, 385.01, 385.101; 428/131–140, 170–172

(56) References Cited

U.S. PATENT DOCUMENTS 3,945,386 A * 3/1976 Anczurowski et al. ...... 604/370
3,967,623 A * 7/1976 Butterworth et al. ....... 604/370
5,533,991 A * 7/1996 Kirby et al. ................. 604/383
5,613,962 A * 3/1997 Kenmochi et al. .......... 604/378

FOREIGN PATENT DOCUMENTS

| JP | 1-201569 | 8/1989 |
|----|----------|--------|
| JP | 2-221450 | 9/1990 |
| JP | 04312431 | 11/1992 |
| JP | 7-232409 | 9/1995 |
| JP | 9-3755 | 1/1997 |
| JP | 9-111631 | 4/1997 |

* cited by examiner

*Primary Examiner*—Jacqueline Stephens
(74) *Attorney, Agent, or Firm*—Birch, Stewart, Kolasch & Birch, LLP (57) ABSTRACT

A topsheet 10 for an absorbent article comprising a first fiber layer 1 disposed on the side of a wearer and a second fiber layer 2 disposed on the side of an absorbent member, the first fiber layer 1 and the second fiber layer 2 being partially bonded together at joints 3 in a prescribed pattern, the first fiber layer 1 having protrusions 4 on the wearer's side in portions other than the joints 3, and the second fiber layer 2 being a fiber aggregate containing heat shrinkable fiber and having heat shrunken parts 5 that have shrunken and densified parts 6 that have been inhibited from heat shrinkage.

6 Claims, 7 Drawing Sheets

TOPSHEET FOR ABSORBENT ARTICLE

FIELD OF THE INVENTION

The present invention relates to a topsheet to be used in absorbent articles, such as sanitary napkins, panty liners, incontinence pads, and disposable diapers, on the side to be brought into contact with a wearer's body.

BACKGROUND OF THE INVENTION

A topsheet used in absorbent articles, such as sanitary napkins and disposable diapers, is required to have not only absorbing performance for smoothly passing liquid body waste, e.g., menstrual blood or urine, to an underlying absorbent member but surface characteristics for causing neither discomfort due to overhydration nor skin troubles such as an itch and a rash.

To meet these requirements various topsheets with an uneven surface on the wearer's side have been proposed for application to absorbent articles.

JP-A-9-111631 discloses wrinkled nonwoven fabric with a great number of streaky wrinkles (ridges) arrayed on its surface, which is used as a topsheet of an absorbent article such as a disposable diaper or a sanitary napkin. The wrinkled nonwoven fabric is produced by superposing a heat non-shrinkable fiber layer on a layer comprising heat shrinkable fiber and heat bondable fiber whose melting point is lower than the shrinkage starting temperature of the heat shrinkable fiber, joining the two layers by applying heat in stripes, and shrinking the fiber layer containing the shrinkable fiber to deform the other fiber layer. Because the shrunken fiber layer has an increased thickness, the whole sheet lacks sufficient softness. Further, the structure is not such that allows the liquid discharged on the surface to quickly migrate into the underlying absorbent member. As a result, the liquid tends to remain on the surface to cause overhydration or skin troubles. When this sheet is used as a topsheet of a sanitary napkin, the color of remaining blood is noticeable, giving a dirty impression to a user.

JP-A-7-232409 discloses composite nonwoven fabric composed of a textured synthetic resin film with a grain pattern and an extensible nonwoven fabric. Having a grain pattern, the composite fabric is soft and matte. However, the fabric easily bunches up, and the resin film side easily makes large wrinkles when bent. Therefore, an absorbent article having the composite fabric as a topsheet comes to have poor fit to a wearer's body, and liquid is apt to flow along the wrinkles to cause a leak. Where, in particular, used as a topsheet of a sanitary napkin, which is usually packaged as folded into three, wrinkles occur easily to invite leakage.

JP-A-9-3755 discloses nonwoven fabric with a textured surface designed to serve as a female member of a mechanical fastener in disposable diapers, etc., which is produced by superposing a layer containing heat shrinkable fiber and a layer containing heat non-shrinkable fiber, and heat embossing the two layers thereby bonding the two layers in parts and simultaneously causing the layer containing the heat shrinkable fiber to shrink.

In nonwoven fabrics of the type which are produced by joining a layer comprising heat shrinkable fiber and a layer comprising non-shrinkable fiber and shrinking the layer comprising heat shrinkable fiber, such as those proposed in JP-A-9-111631 and JP-A-8-3755 described supra, a web or nonwoven fabric is used as the layer comprising heat shrinkable fiber. A web needs care in handling because it tears easily due to low strength and also fuzzes easily. Nonwoven fabric, on the other hand, should be produced without involving heat application. Nonwoven fabrics fabricated with no heat application include needle punch nonwoven, spunlace nonwoven, and resin bond nonwoven. Such nonwoven products are costly because of low production speeds, as seen from the fact that their application has been limited to relatively expensive cataplasms. Besides, it is difficult to produce nonwoven products of small basis weight by these nonwoven techniques.

JP-A-1-201569 proposes bulky reinforced nonwoven fabric composed of a fiber web and monofilaments fixed to the web, the monofilaments having shrunken to wrinkle the web. The monofilaments are not a fiber layer having high densified parts which is used in the present invention. JP-A-2-221450 teaches a process of making highly extensible nonwoven fabric comprising heat treating a web of self-crimping conjugate fiber. According to the process, the heat treatment is carried out simultaneously with embossing so that the resulting nonwoven fabric is a shrunken product.

SUMMARY OF THE INVENTION

An object of the present invention is to provide a topsheet for absorbent articles which is capable of quickly passing discharged body liquid, such as blood or urine, to an absorbent member, has softness, and hardly bunches up or wrinkles.

Another object of the present invention is to provide a process of efficiently producing the topsheet by using a heat shrinkable nonwoven fabric which has sufficient strength not to tear during handling, is produced at a low cost, and may have an arbitrary basis weight from small to large.

The object of the present invention is accomplished by a topsheet for an absorbent article comprising a first fiber layer disposed on the side of a wearer and a second fiber layer disposed on the side of an absorbent member, the first fiber layer and the second fiber layer being partially bonded together at joints in a prescribed pattern, the first fiber layer having protrusions on the side of a wearer in portions other than the joints, and the second fiber layer being a fiber aggregate containing heat shrinkable fiber and having heat shrunken parts that have shrunken and densified parts that have been inhibited from heat shrinkage.

The present invention also provides a process of producing the topsheet for absorbent articles which comprises heat embossing a fiber aggregate containing heat shrinkable fiber to form a second fiber layer-forming material having densified parts, superposing a fiber aggregate as a first fiber layer-forming material on one side of the second fiber layer-forming material, partially joining the first fiber layer-forming material and the second fiber layer-forming material, and shrinking the second fiber layer-forming material by heat treatment.

The present invention also provides a preferred embodiment of the process of producing the topsheet for absorbent articles, wherein the fiber aggregate containing heat shrinkable fiber is a web, and the step of forming a second fiber layer-forming material having densified parts (i.e., a heat shrinkable nonwoven fabric containing heat shrinkable fiber in the heat shrinkable state and having part of its constituent fiber fusion bonded in parts by embossing) is carried out by partially fusion bonding the constituent fiber of the web at or above the shrinkage starting temperature of the heat shrinkable fiber with a heat embossing machine while applying tension to the web, and continuing applying tension to the web having passed through the embossing machine until the temperature of the heat shrinkable fiber of the web reduces lower than the shrinkage starting temperature of the heat shrinkable fiber.

BRIEF DESCRIPTION OF THE DRAWINGS

The present invention will be more particularly described with reference to the accompanying drawings, in which.

DETAILED DESCRIPTION OF THE PREFERRED EMBODIMENTS

The present invention will be described in greater detail with reference to its preferred embodiments.

Figure 1:
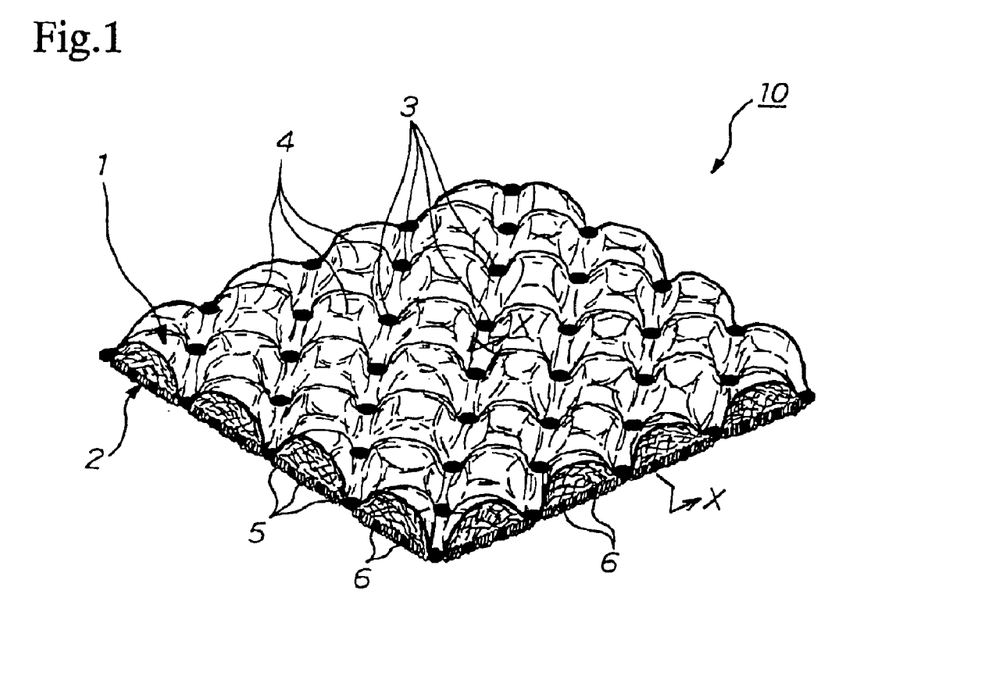
FIG. 1 is a perspective of an example of the topsheet according to the present invention.
Figure 2:
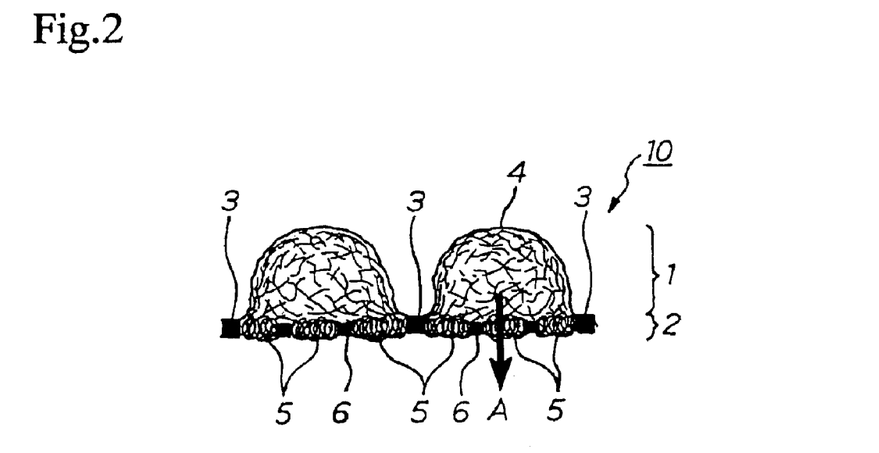
FIG. 2 is an exaggerated cross-sectional view of the topsheet of FIG. 1, taken along line X—X.

An embodiment of the topsheet according to the present invention is shown in FIG. 1. FIG. 2 presents a schematic cross-section of the topsheet shown in FIG. 1, taken along X—X line. The topsheet 10 shown in FIG. 1 consists of a first fiber layer 1 disposed on the side of a wearer and a second fiber layer 2 disposed on the side of an absorbent member of an absorbent article. The first fiber layer 1 and the second fiber layer 2 are each made of a fiber aggregate and are partially joined together at joints 3 in a prescribed pattern.

Figure 4A:
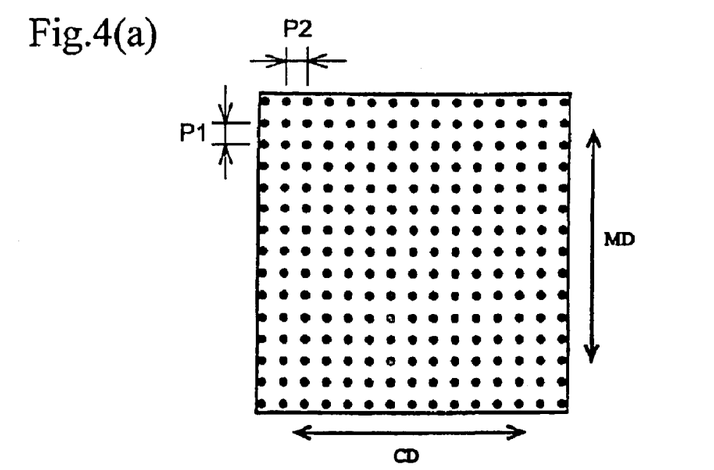
FIG. 4(a) shows an example of a pattern of densified parts.
Figure 4B:
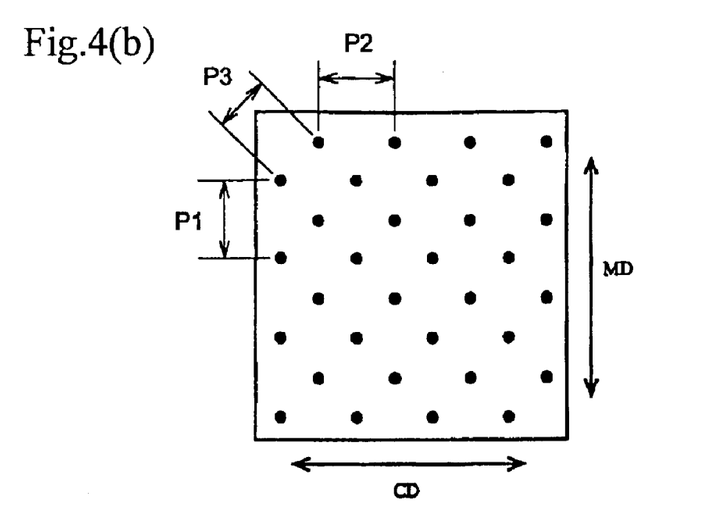
FIG. 4(b) shows another example of a pattern of joints.

In this embodiment, the joints 3 are discretely arranged in a lattice pattern in their plan view as illustrated in FIG. 4(b). The topsheet 10 is densified at the joints 3 to have a smaller thickness and a larger density than at other parts.

The joints 3 are formed by various joining means, such as heat embossing, ultrasonic embossing, and bonding with an adhesive. The individual joints 3 may have an arbitrary shape, such as a circular shape as adapted in this particular embodiment, an elliptic shape, a triangular shape, a rectangular shape or a combination thereof The joints 3 may be continuously formed to make a line pattern, such as a pattern of straight lines, curved lines, and intersecting straight lines.

Figure 3A:
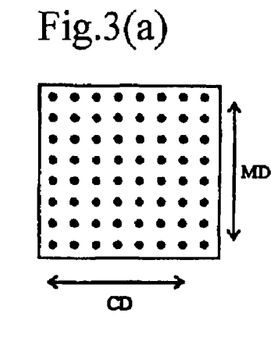
FIG. 3(a), FIG. 3(b) and FIG. 3(c) show examples of a pattern of joints.
Figure 3B:
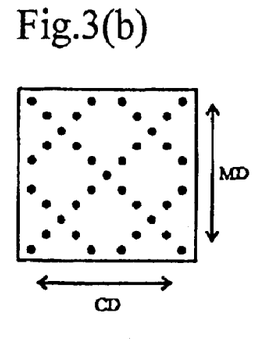
Figure 3C:
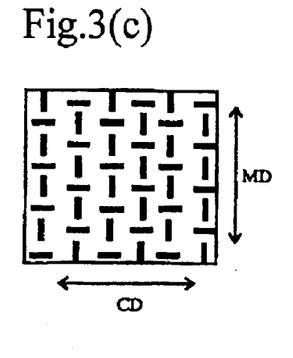

Examples of conceivable joints patterns other than the pattern of FIG. 4(b) are shown in FIGS. 3(a)–3(c).

The first fiber layer 1 is made of a fiber aggregate. The portions of the first fiber layer other than the joints 3 with the second fiber layer 2 are protruded toward the wearer's side. That is, as illustrated in FIGS. 1 and 2, every portion between adjacent joints 3 (more specifically every rectangular portion having the joints 3 at its four corners) has a dome-shaped protrusion. As a whole, the topsheet 10 has a large number of protrusions 4 on its side adapted to face a wearer. Each protrusion 4 is filled with the fiber constituting the first fiber layer 1. In the portions where the first fiber layer 1 forms protrusions, the first fiber layer 1 and the second fiber layer 2 are not bonded together but are in close contact with each other over the entire area. The shape of the protrusions 4 depends chiefly on the form of the fiber aggregate as a first fiber layer-forming material and the pattern of the joints 3.

The first fiber layer 1 is an aggregate of fiber different from the fiber making up the second fiber layer 2 in kind and/or composition.

The second fiber layer 2 is a fiber aggregate containing heat shrinkable fiber, which includs a fiber aggregate consisting solely of heat shrinkable fiber, and has shrunken parts 5 that have been heat shrunk and densified parts 6 that have been inhibited from heat shrinkage. The densified parts 6 exist independently of the joints 3 between the first and the second fiber layers and have a higher density than the shrunken parts 5.

The heat shrinkable fiber making up the second fiber layer 2 has heat shrunken in the shrunken parts 5 but has been inhibited from shrinkage in the densified parts 6. In other words, the heat shrinkable fiber in the densified parts 6 has not substantially shrunken or, if it has undergone heat shrinkage, the degree of the shrinkage is extremely smaller than that of the fiber in the shrunken parts 5.

The topsheet 10 of the present embodiment is of the type that is obtained by the process of the present invention, in which a fiber aggregate (before shrinkage) for forming the second fiber layer 2 is previously heat embossed to form the densified parts 6 and then subjected to heat shrinkage to form the shrunken parts 5. Therefore, the fiber aggregate in the shrunken parts 5 has gained in thickness on shrinkage, whereas the fiber aggregate in the previously densified parts 6 has been prevented from shrinking and increasing its thickness. As a result, the second fiber layer is thinner and denser in the densified parts 6 than in the shrunken parts 5. The shrunken parts 5 exhibit extensibility, whereas the densified parts 6 have substantially no or much less extensibility than the shrunken parts 5.

It is preferred that the heat shrinkable fibers in the densified parts 6 be in a fusion bonded state so that the densified parts 6 may not be destroyed and the topsheet may be kept in good shape condition even when the topsheet is deformed in conformity with wearer's movement while worn.

The densified parts 6 can be formed by, for example, (1) subjecting a fiber aggregate (a fiber aggregate before shrinkage) to heat embossing or ultrasonic embossing or (2) partially applying a hot-melt adhesive to the fiber aggregate.

The individual densified parts 6 according to the present embodiment have a circular shape and are discretely arranged at regular intervals in both the machine direction (MD) and the cross direction (CD) to form a regular dot pattern as shown in FIG. 4(a). The densified parts 6 are arranged at a smaller pitch than the joints 3 so that the topsheet 10 has at least one densified part 6, preferably at least two densified parts 6, per protrusion 4 (i.e., per rectangle having the joints 3 at the four corners). The pattern of the densified parts 6 includes, in addition to the dot pattern, straight lines, curved lines (including continuous waves), lattices, and zigzags. The dot may have arbitrary shapes, such as circles, triangles, and rectangles.

The ratio of the total area of the joints 3 to the area of the topsheet 10 which is measured before shrinking the second fiber layer-forming material, hereinafter referred to as an area ratio R1, is preferably 2 to 15%, still preferably 5 to 10%, in order to assure bonding between the two fiber layers 1 and 2 while allowing the first fiber layer 1 to rise to form the projections 4 with sufficient height for bulkiness.

The ratio of the total area of the densified parts 6 to the area of the topsheet 10 which is measured before joining to the first fiber layer-forming material and before shrinkage, hereinafter referred to as an area ratio R2, is preferably 15 to 40%, still preferably 20to 35%, in order for at least one densified part 6 to exist between every two adjacent joints 3 after shrinkage.

The topsheet 10 of the present embodiment have the following advantages, which are particularly attributed to the densified parts 6 of the second fiber layer 2 that have been inhibited from heat shrinkage.

(1) The second fiber layer has its thickness reduced as a whole. There is a density difference between the first fiber layer and the second fiber layer so that liquid such as blood and urine migrates to an absorbent member quickly. Not being allowed to remain on the surface of the topsheet, the liquid neither causes overhydration and skin troubles nor gives a dirty impression to a user. The density difference is a difference in density between the protrusions 4 of the first fiber layer 1 where fibers are sparse and the shrunken parts 5 of the second fiber layer 2 that are dense. This density difference effectively makes the liquid discharged on the topsheet migrate to an underlying absorbent member as shown by arrow A in FIG. 2.

(2) A dense network structure is formed of heat shrinkable fiber, in which the densified parts 6 and the joints 3 are connected via the shrunken parts 5. The topsheet having such a network structure hardly bunches or wrinkles.

(3) The densified parts 6 which have been formed before shrinkage serve to control the thickness gain of the second fiber layer-forming material on shrinkage and therefore to secure softness of the whole sheet and wearing comfort as an absorbent article.

The first fiber layer is preferably made up of fiber comprising a thermoplastic polymer. Useful thermoplastic polymers include polyolefins, such as polyethylene and polypropylene; polyesters, such as polyethylene terephthalate; and polyamides. Conjugate fibers composed of these thermoplastic polymers, such as core-sheath conjugate fiber and side-by-side conjugate fiber, are also useful.

Forms of the fiber aggregate as a first fiber layer include carded webs, thermal bond nonwovens, water needle nonwovens, needle punch nonwovens, solvent bond nonwovens, spunbond nonwovens, melt-blown nonwovens, and knitted fabric.

The first fiber layer is preferably formed of a carded web. A carded web, having fibers oriented relatively randomly, rises easily on shrinkage of the second fiber layer-forming material and forms protrusions having a relatively small fiber density. Further, a carded web can previously have the intersections of constituent fibers fused together to a moderate extent by heat treatment to provide a topsheet with a non-fuzzing and soft surface.

A carded web is a fiber aggregate before being made into nonwoven fabric, i.e., a very loose aggregate of fibers that has not been subjected to a post treatment for making nonwovens, such as heat fusion treatment by an air-through process or a calendering process. Where a carded web is used as a first fiber layer-forming material, the fibers of the carded web are bonded to each other by fusion bonding or with a solvent or mechanically entangled with each other either simultaneously with or after joining with the second fiber layer-forming material.

The second fiber layer comprises heat shrinkable fibers, particularly those comprising thermoplastic polymers. Self-crimping fiber is particularly preferred for the capability of absorbing liquid and of extending even after shrinkage thereby assuring softness of the topsheet as a whole. Self-crimping fiber can be handled similarly to ordinary fiber for nonwovens before heat application and, when heated at a given temperature, crimps itself in a helical form. Self-crimping fiber having such characteristics exhibits both heat shrinkability and elastomeric behaviors after shrinkage.

Self-crimping fibers include conjugate fibers consisting of two thermoplastic polymers having different shrinkage characteristics in an eccentric core-sheath configuration or a side-by-side configuration. Examples of such self-crimping conjugate fibers are given in JP-A-9-296325 and Japanese Patent 2759331. A combination of an ethylene-propylene random copolymer and polypropylene is an example of suitable thermoplastic polymers having different percent shrinkages.

The fiber aggregate as the second fiber layer-forming material includes (1) a carded web containing self-crimping fiber and (2) heat shrinkable nonwoven fabric, such as thermal bond nonwoven, water needle nonwoven, needle punch nonwoven, solvent bond nonwoven, spunbond nonwoven, and melt-blown nonwoven. The term "heat shrinkable nonwoven fabric" as used herein means nonwoven fabric which shrinks on heating at a prescribed temperature.

The first or second fiber layer may contain fibers other than the above-mentioned fibers, for example, water-absorbing fibers, such as rayon, cotton, and hydrophilic acrylic fiber. For example, the second fiber layer may contain heat bondable fiber and other fibers. Heat bondable fiber is incorporated for the purpose of stabilizing the shape of the topsheet and enhancing resistance against bunching or wrinkling.

The fiber aggregate as a second fiber layer-forming material preferably contains heat shrinkable fiber in a proportion of 30 to 100% by weight, particularly 50 to 100% by weight. As long as the heat shrinkable fiber content is 30% by weight or more, the second fiber layer-forming material exhibits sufficient deformability on shrinkage for causing the non-joined portions of the first fiber layer-forming material to form protrusions having a reduced fiber density.

The fiber aggregate as a first fiber layer-forming material preferably contains 50 to 100% by weight, particularly 70 to 100% by weight, of a fiber that does not shrink at the shrinkage starting temperature of the heat shrinkable fiber of the second fiber layer-forming material. As long as the content of such a fiber is 50% by weight or higher, the first fiber layer-forming material becomes a first fiber layer having a lower fiber density relative to the shrunken parts of the second fiber layer.

While the first fiber layer-forming material may contain the heat shrinkable fiber used in the second fiber layer-forming material, it is desirable that the heat shrinkable fiber content in the first fiber layer-forming material be lower than that in the second fiber layer-forming material so as to form a first fiber layer with a relatively lower fiber density than that of the shrunken parts of the second fiber layer. By this design, the second fiber layer-forming material shrinks to a higher degree than the first fiber layer-forming material, and the first fiber layer-forming material rises on shrinkage. The heat shrinkable fiber, if present in the first fiber layer-forming material, shrinks into a helical form to extend the interfiber distance, facilitating creating portions with sparse fiber in the first fiber layer.

Figure 5A:
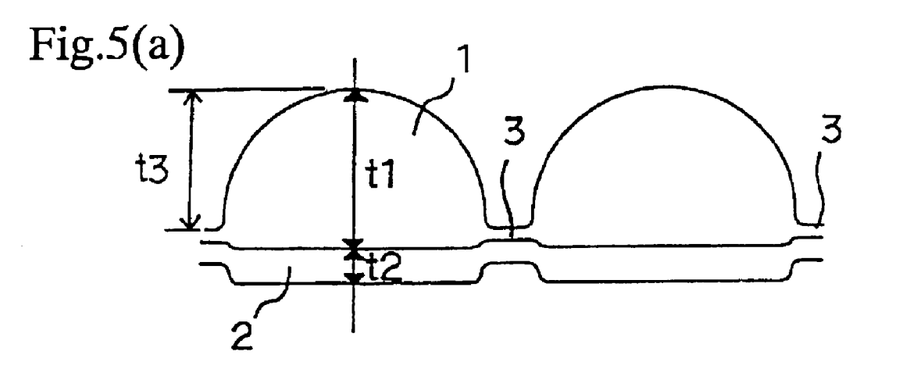
FIG. 5(a) is a schematic of FIG. 2 which indicates dimensions used in measuring apparent thickness and protrusion height.

The first fiber layer 1 of the topsheet 10 preferably has an apparent thickness (t1, see FIG. 5(a)) of 0.1 to 3 mm, particularly 0.5 to 2.5 mm. The second fiber layer 2 of the topsheet 10 preferably has an apparent thickness (t2, see FIG. 5(a)) of 0.2 to 1.5 mm, particularly 0.5 to 1.5 mm.

With an apparent thickness t1 of 0.1 mm or larger, there will be a sufficient volume capable of being deformed under body pressure to give a fluffy and soft feel to a wearer. With t1 of 3 mm or smaller, the distance that the liquid entering the protrusions must travel to reach the second fiber layer 2 is short enough for assuring smooth absorption even under low body pressure.

With an apparent thickness t2 of 0.2 mm or larger, non-uniformity of fiber distribution in the second fiber layer 2 is avoided. The topsheet of the present invention is designed to create capillary force by a fiber density difference between the first and second fiber layers, which is made use of to develop such absorptivity that does not allow liquid to remain on the surface. If there is a non-uniform fiber distribution in the second fiber layer, it would be difficult to make a sufficiently dense structure. With t2 of 1.5 mm or smaller, the second fiber layer, being less compact than the absorbent member, accelerates liquid migration to the absorbent member and reduces the amount of the liquid remaining in the second fiber layer. As a result, the topsheet has improved properties of hiding the color of the excreted liquid and effectively prevents backflow of the liquid.

Taking wearing comfort and absorptivity into consideration, the height t3 (see FIG. 5(a)) of the protrusions 4 is preferably 0.5 to 5 mm, particularly 0.5 to 3 mm. With a height t3 of 0.5 mm or larger, the contact area with the skin is reduced to prevent overhydration or a rash which might be caused by intimate contact of the skin with the topsheet. A height t3 of 5 mm or smaller, the distance the absorbed liquid must migrate to the second fiber layer 2 is short enough to make the liquid be absorbed smoothly even under low body pressure.

The apparent thickness of the first and the second fiber layers can be measured as follows. A 30-mm square cut out of a topsheet is cut along a line substantially parallel with the longitudinal direction, namely, the fiber orientation direction (the MD) of the nonwoven fabric making the first fiber layer, and passing through the joints 3. A magnified photograph is taken of the cut area under a microscope SZH10 supplied by Olympus Optical Co., Ltd. The real maximum thickness of the first fiber layer, calculated from the magnification, is taken as the apparent thickness t1 of the first fiber layer. The thickness of the second fiber layer at the same position of measuring the first fiber layer maximum thickness is taken as the apparent thickness t2 of the second fiber layer. In other words, the thickness of the first and the second fiber layers are measured on the same straight line extending in the sheet thickness direction (see FIG. 5(a)). The protrusion height t3 is the height of from the bottom of a depression to the apex of a protrusion as measured in the same manner as for thickness t1 and t2.

In the topsheet 10, the second fiber layer 2 has a higher apparent fiber density than the first fiber layer 1. The apparent fiber density d1 of the first fiber layer 1 is preferably 0.001 to 0.05 g/cm$^3$, more preferably 0.001 to 0.02 g/cm$^3$, still more preferably 0.005 to 0.015 g/cm$^3$, and the apparent fiber density d2 of the second fiber layer 2 is preferably 0.01 to 0.2 g/cm$^3$, still preferably 0.02 to 0.15 g/cm$^3$.

Where the apparent fiber densities d1 and d2 fulfill the above-described relationship, liquid discharged on the topsheet 10 swiftly enters the first fiber layer 1, and the liquid in the first fiber layer 1 then migrates smoothly to the second fiber layer 2 by virtue of the fiber density difference. As a result, overhydration, skin troubles such as an itch and a rash, and wearing discomfort which might occur due to liquid remaining on the surface of the topsheet can be prevented more effectively.

If the apparent fiber density d1 is less than 0.001 g/cm$^3$, the fibers are so sparse to have too much freedom of movement that the surface of the topsheet is liable to fuzz up. With d1 more than 0.05 g/cm$^3$, it is difficult to make an effective density difference from the second fiber layer enough to produce a sufficient capillary force.

If the fiber density d2 of the second fiber layer is smaller than 0.01 g/cm$^3$, the second fiber layer tends to fail to have such a dense structure as to develop a sufficient capillary force. As a result, liquid is prone to remain on the surface, and the topsheet has reduced hiding properties (low cleanliness feel). The second fiber layer with d2 exceeding 0.2 g/cm$^3$ is too dense for securing smooth absorption, causing the liquid remaining problem.

For making the sparse-dense structure of the first and second fiber layers to develop a sufficient capillary force, the ratio of the apparent fiber density d2 to the apparent fiber density d1, d2/d1, is preferably 1.2 or higher, still preferably 3 to 10.

The apparent fiber densities of the first layer fiber 1 and the second fiber layer 2 are measured as follows. A 30 mm-square cut out of a topsheet sample is cut along a line substantially parallel with the fiber orientation direction of the first fiber layer, namely, the MD of the nonwoven fabric making the first fiber layer, and passing through the joints 3. The apparent thickness t1 (mm) of the first fiber layer is measured in the manner described supra.

Figure 5B:
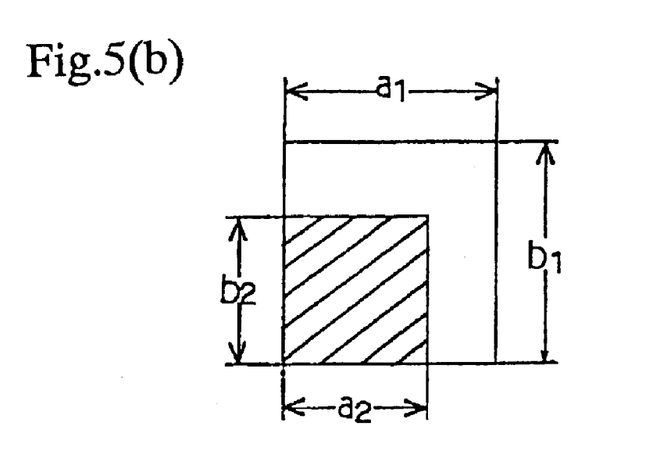
FIG. 5(b) is a schematic indicating dimensions used in measuring percent area shrinkage.

The percent area shrinkage (A; %) of the sample is calculated from the area of the first fiber layer-forming material measured before shrinkage (before joining of the first and second fiber layers), represented by $a_1 \times b_1$ (see FIG. 5(b)), and the area of the first fiber layer measured after joining with the second fiber layer-forming material and shrinking the second fiber layer-forming material, represented by $a_2 \times b_2$ (see FIG. 5(b)), according to equation: $A=[(a_1 \times b_1 - a_2 \times b_2)/(a_1 \times b_1)] \times 100$. The basis weight P2 (g/m$^2$) of the first fiber layer is calculated from the area shrinkage A (%) and the basis weight P1 (g/m$^2$) of the first fiber layer before joining to the second layers and shrinking according to equation: $P2=P1 \times 100/(100-A)$. The apparent fiber density d1 (g/cm$^3$) of the first fiber layer is obtained from equation: $d1=P2 \times (1/1000) \times (1/t1)$.

The apparent fiber density d2 of the second fiber layer 2 is obtained in the same manner as for d1. In the calculations, the apparent thickness t2 of the second fiber layer 2 is obtained in the same manner as for the t1.

The topsheet 10 preferably has a basis weight of 20 to 80g/m$^2$, particularly 20 to 60 g/m$^2$, for minimizing the material cost and for assuring flexibility of the whole sheet.

The basis weight of the topsheet is obtained by weighing a specimen of at least 50 mm by 50 mm cut out of a topsheet sample with an electronic balance (minimum reading: 1 mg) and calculating a weight per unit area (m$^2$).

The topsheet 10 for absorbent articles preferably shows a through-thickness deformation of 0.03 to 0.3 mm/gf/cm$^2$, particularly 0.04 to 0.2 mm/gf/cm$^2$, when compressed under a load of 10 gf/cm$^2$. With a through-thickness deformation of 0.03 mm or more, the topsheet is capable of sufficient deformation in the thickness direction even under low pressure applied to provide a wearer with a fluffy and soft feel. A topsheet with a through-thickness deformation of 0.3 mm or less assures softness without increasing the thickness considerably and yet is free from such a problem that the fibrous structure (interstices among fibers) may have too much freedom of deformation to retain the original structure as designed and to keep the excellent absorbing performance.

The through-thickness deformation per gf/cm$^2$ in compression under 10 gf/cm$^2$ is obtained as follows. Measurement is made with a compression tester KES-FB3, supplied by Katotec. The tester has a disk indenter having a compressing area of 2 cm$^2$. The disk indenter is vertically moved to give a compression-recovery load to such a sample as fabric or film to obtain a compression load-compressive deformation hysteresis loop for the compression-recovery cycle, which furnishes compression data, such as the sample thickness, the compression work done, the recovery properties, and the like.

More concretely, a 2.5 cm-side square specimen is cut out of the topsheet and set on KES-FB3. The disk indenter is moved down at a speed of 0.02 mm/sec to apply a compression load up to 50 gf/cm$^2$, at which the manual return switch is pushed to switch the downward movement to upward movement. The disk indenter is lifted until the load decreases to zero. A hysteresis loop for the compression-recovery cycle is plotted, from which the thickness t4 under a 10 gf/m$^2$ load in the process of compression is obtained. The thickness under a 0.5 gf/cm$^2$ load being taken as an initial thickness (t5), a thickness reduction (t5-t4) (mm) is calculated, and the calculated thickness reduction is divided by 10, thereby obtaining a thickness deformation per gf/cm$^2$.

It is preferred for the topsheet of the present invention to have a surface whiteness of 60 or higher in terms of L value (hereinafter referred to as L1) and a red plate hiding ratio of 35% or higher, preferably 40% or higher.

The topsheet 10 which has an L value (L1) of 60 or higher is equal to conventional film type topsheets in color hiding performance and capability of providing a clean impression (invisibility of the color of absorbed liquid). The L value represents the capabilities of covering the liquid (blood) having been absorbed and spread in the absorbent member. The closer the L value to 100, the whiter the sheet looks.

The L value (L1) and the red plate hiding ratio of the topsheet are measured as follows.

Measurement of L Value of Topsheet (L1):

A color difference meter SZ-Σ80 supplied by Nippon Denshoku Industries, Co., Ltd. is used after calibration with a white reference plate. A light emitting pipe of 30 mm in diameter and a sample mount of 30 mm in diameter are chosen. A specimen of the topsheet is put on the glass mount with its side to be measured (the side coming into contact with a wearer) facing the light source. A specimen holder (black plate) attached to the instrument is placed on the specimen (opposite to the side to be measured). Five specimens cut out of different parts of a sample are measured, and the readings are averaged to yield the L value (surface whiteness) of the sample.

Measurement of Red Plate Hiding Ratio:

Measurements are taken in the same manner as for the L value, except for replacing the black specimen holder with the red plate attached to the instrument. First of all, the red side of the red plate (with no specimen) is measured to prepare a spectral curve, and the reflectance Ra at a selected wavenumber of 500 cm$^{-1}$ is recorded. Then, a specimen is placed between the glass and the red plate with the side to be measured facing the light source. Five specimens cut out of different parts of a sample are measured to obtain an average reflectance Rb at 500 cm$^{-1}$. A red plate hiding ratio is calculated from equation:

Red plate hiding ratio $(\%)=[(Rb-Ra)/(100-Ra)]\times 100$

The process of producing the topsheet of the present invention will be described with particular reference to the above-described topsheet 10. FIGS. 6(a) through 6D are referred to.

Figures 6A, 6B, 6C, 6D:
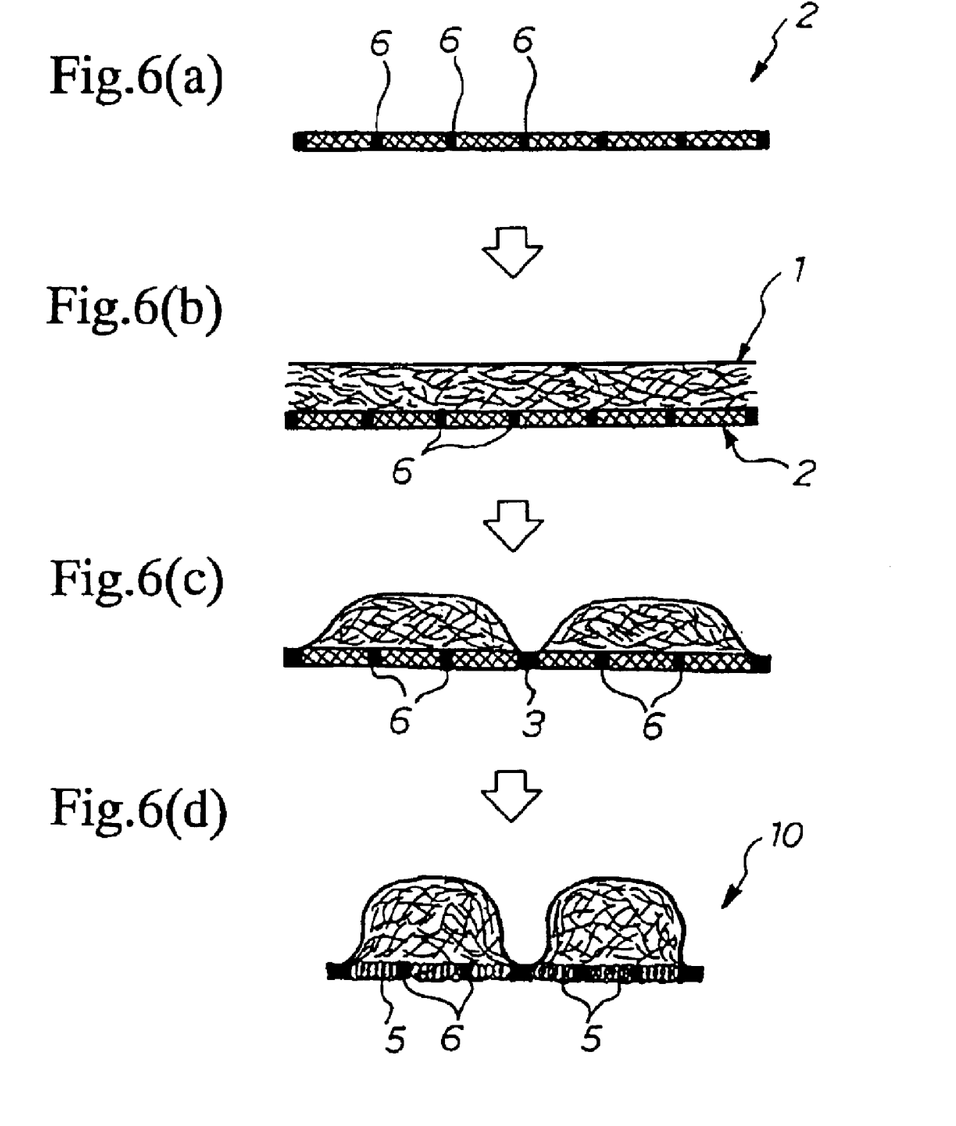
FIGS. 6(a), 6(b), 6(c) and 6(d) are a flow diagram showing the process for producing a topsheet according to the present invention.

As shown in FIG. 6(a), a fiber aggregate containing a heat shrinkable fiber is heat embossed to form a second fiber layer-forming material 2 having densified parts 6.

As shown in FIG. 6(b), another fiber aggregate (a first fiber layer-forming material) is superposed on the second fiber layer-forming material. As shown in FIG. 6C, the two fiber aggregates are partly joined to form joints 3 in a prescribed pattern.

As shown in FIG. 6D, the joined fiber aggregates are heat treated at or above the shrinkage starting temperature of the heat shrinkable fiber (the temperature at which the heat shrinkable fiber of the second fiber layer-forming material starts to shrink) to cause the second fiber layer-forming material to shrink. Thus, the portions of the first fiber layer-forming material other than the joints 3 rise to produce a topsheet 10 having protrusions 4.

From the standpoint of heat shrinkage controllability, extension recovery and compressive deformability of the resulting topsheet, and bulkiness resulting from formation of the protrusions, the percent heat shrinkage S (%) of the second fiber layer-forming material preferably ranges from 20 to 90%, particularly 40 to 80%. The term "percent heat shrinkage" as referred to here means a percent area shrinkage which is calculated from the original area $S_0$ and the area $S_1$ after shrinkage according to equation:

$S(\%)=[(S_0-S_1)/S_0]\times 100$

The means for shrinking the second fiber layer-forming material includes a table dryer and air-through heating equipment used in the fabrication of thermal bond nonwoven.

The second fiber layer-forming material having densified parts 6 (see FIG. 6(a)), which is obtained by heat embossing a fiber aggregate containing heat shrinkable fiber, is a heat shrinkable nonwoven fabric containing heat shrinkable fiber in its shrinkable state and having part of its constituent fibers heat fusion bonded by the heat embossing treatment. Such a heat shrinkable nonwoven fabric having densified parts will be referred to simply as a "heat shrinkable nonwoven fabric".

The heat shrinkable nonwoven fabric as a second fiber layer-forming material will be described with reference to its preferred embodiment. The heat shrinkable nonwoven fabric typically has a single layer structure. The term "single layer structure" as used herein is intended to include nonwoven fabrics prepared by superposing two or more webs on each other in which the constituent fibers are not bonded at their intersections. The heat shrinkable nonwoven fabric contains heat shrinkable fiber. The heat shrinkable fiber is in a state capable of heat shrinking after being formed into a nonwoven fabric and before being heated, not to speak of before being formed into a nonwoven fabric. The phrase "a state capable of heat shrinking" is used to include a state that the fiber has not yet been given heat and is capable of shrinking on heat application and a state that the fiber has been given heat under such a condition as to inhibit shrinkage and still has capability of shrinking on heat re-application. Where the heat shrinkable nonwoven fabric is composed of two or more webs, it is sufficient that at least one of the webs contains heat shrinkable fiber.

The heat shrinkable fiber includes any kinds of known heat shrinkable fibers, such as an ethylene-propylene random copolymer (EP) fiber. Heat shrinkable core-sheath conjugate fiber having an EP as a core and a heat bondable resin, e.g., polypropylene (PP) as a sheath is also useful.

Self-crimping fiber is a particularly preferred heat shrinkable fiber for its capability of developing extensibility after heat shrinkage. Examples of suitable self-crimping fibers have been recited supra as a fiber constituting the second fiber layer.

The heat shrinkable fiber may be staple fiber (short fiber) or filaments (long fiber). Short fiber is preferred for providing a good texture after heat shrinkage. Short fiber having a fiber length of 5 to 100 mm, particularly 30 to 60 mm is still preferred for web-forming properties (carding capabilities) and non-fuzzing properties. The heat shrinkable fiber preferably has a thickness of about 1 to 10 dtex, particularly about 1.5 to 4 dtex, for providing a good texture and a good balance of fiber structure. The shrinkage starting temperature $T_s$ of the heat shrinkable fiber can be selected from a range, e.g., of from 90 to 110C. The term "shrinkage starting temperature" as used herein denotes a measured temperature of an oven capable of elevating temperature at which a fiber put in the oven substantially starts shrinking. In Preparation Examples hereinafter given, a heat shrinkable fiber whose $T_s$ was about 90° C. as used.

The heat shrinkable nonwoven fabric may contain other fibers in addition to the heat shrinkable fiber. The other fibers include heat bondable fibers. In order to improve the strength of the nonwoven fabric while retaining shrinkability, the heat shrinkable nonwoven fabric preferably comprises 10 to 70% by weight, particularly 30 to 50% by weight, of the heat bondable fiber and 30 to 90% by weight, particularly 50 to 70% by weight, of the heat shrinkable fiber based on the total weight of the nonwoven fabric.

It is preferred for the fibers constituting the heat shrinkable nonwoven fabric other than the heat shrinkable fiber to have melting points higher than the shrinkage starting temperature $T_s$ of the heat shrinkable fiber so that the resulting heat shrinkable nonwoven fabric may be prevented from fuzzing up and exhibit a satisfactory texture. The term "melting point" as used herein means the maximum peak temperature in a DSC (differential scanning calorimetry) curve prepared in measurement of heat of fusion of a polymer with a DSC. Where the fiber other than the heat shrinkable fiber is a multi-component conjugate fiber, the lowest of the melting points of the constituent resins is taken as the "melting point" of the fiber.

The heat shrinkable nonwoven fabric has part of its constituent fiber fusion bonded by heat embossing to form fusion bonded parts. The fusion bonded parts are preferably such that are formed by melting followed by solidification of a heat fusible resin having a higher melting point than the shrinkage starting temperature $T_s$ of the heat shrinkable fiber. In this case, the resulting heat shrinkable nonwoven fabric is prevented from fuzzing and provides a good texture. The fusible resin is preferably present as a component making up a multi-component heat shrinkable fiber or in the form of a fusion bondable fiber that is incorporated independently of the heat shrinkable fiber.

The heat embossing is carried out with an embossing machine having two pressing members facing each other at least one of which can be heated to a prescribed temperature. One of the pressing members has its surface engraved in a prescribed pattern of projections and depressions, and the other has a smooth surface. The pattern causing partial fusion is not particularly limited. Taking into consideration ease of shrinking and the texture after shrinking, a pattern of independent dots of circular, triangular, rectangular, hexagonal or like shape is preferred. Too high an area ratio of the fusion bonded parts impairs shrinkability, and too low an area ratio of the fusion bonded parts results in insufficient strength and poor handling properties. From these points of view, the area ratio of the fusion bonded parts is preferably in a range of 5 to 40%, particularly 7 to 30%. Each of the fusion bonded parts preferably has an area of 0.5 to 20mm$^2$, particularly 0.75 to 7.5 mm$^2$. The temperature for fusion bonding is such that causes the constituent fibers to melt and bond to each other sufficiently. It is usually not lower than the softening point of the heat shrinkable fiber contained in the nonwoven fabric. The softening temperature of the heat shrinkable fiber is generally equal to or higher than the shrinkage starting temperature $T_s$ of the heat shrinkable fiber.

The basis weight of the heat shrinkable nonwoven fabric is not critical and subject to wide variation, which is an advantage of using the heat shrinkable nonwoven fabric. The lower limit of the basis weight is about 7 g/m$^2$, preferably about 10 g/m$^2$, while depending on a particular use of the heat shrinkable nonwoven fabric. The upper limit of the basis weight would be about 100 g/m$^2$, preferably about 30 g/m$^2$. The thickness of the heat shrinkable nonwoven fabric is not critical and is usually subject to variation according to the basis weight of the fabric. It is usually about 0.2 to 10 mm, preferably about 0.5 to 3 mm, while depending on a particular use of the heat shrinkable nonwoven fabric.

The heat shrinkable nonwoven fabric is designed to have a maximum percent shrinkage of about 20 to 90%, particularly about 40 to 90%, while varying according to the kind of the heat shrinkable fiber and the area ratio of fusion bonded parts. The maximum percent shrinkage is defined as [(area before shrinkage−area after shrinkage/area before shrinkage)×100] provided that the heat shrinkable nonwoven fabric is heated to the optimum temperature in a free state. In an actual shrinking operation, the heat shrinkable nonwoven fabric does not need to shrink to its maximum percent shrinkage. As far as the object of the present invention is accomplished, the shrinkable nonwoven fabric is made to shrink to a certain degree under appropriate heat treating conditions. Having been heat embossed, the heat shrinkable nonwoven fabric has increased tensile strength (as measured according to JIS L1913.6.3 at a pulling speed of 300 m/min) and thereby improved handling properties. Note that too much enhanced strength may adversely affect the shrinkability and the texture after shrinkage. A suitable tensile strength is about 500 to 2000 gf/50 mm, particularly about 600 to 1400 gf/50 mm, in the MD. The tensile strength is adjustable by controlling the basis weight or the degree of fusion bonding of the nonwoven fabric.

The above-described heat shrinkable nonwoven fabric has various applications. Where used in the production of the topsheet according to the present invention, the heat shrinkable nonwoven fabric can be used as a second fiber layer-forming material, on which a first fiber layer-forming material (a fiber aggregate having no or low heat shrinkability) is superposed. The two layers are joined together and then heat treated to shrink the heat shrinkable nonwoven fabric to form protrusions on the first fiber layer side. In other applications, the heat shrinkable nonwoven fabric is made to shrink either alone or in the form of a composite laminate with other fiber layer(s) to form nonwoven fabric which can be used as a cooking sheet, stuffing of bedding, padding cloth, and the like. The heat shrinkable nonwoven fabric which contains self-crimping fiber as heat shrinkable fiber is also useful as a member other than a topsheet making absorbent articles such as disposable diapers and sanitary napkins, a base sheet of cataplasms, or a sheet for supporting a liquid medicine or a cleaning liquid.

Use of the heat shrinkable nonwoven fabric containing self-crimping fiber as a member making an absorbent article provides the following advantages. An absorbent article such as a disposable diaper usually has a number of elastic members (rubber) attached to a nonwoven fabric member thereof with an adhesive or by heat sealing in order to provide a good fit to a wearer's body. Replacement of such elastic members with the heat shrinkable nonwoven fabric will exclude the use of an adhesive or heat sealing, which leads to cost reduction. Further, production of an absorbent article involving use of elastic members requires expensive equipment, such as a vacuum conveyer, for conveying the product or an intermediate product while preventing them from contracting or curving. Use of the heat shrinkable nonwoven fabric in place of the elastic members excludes the necessity of using such equipment.

Where the heat shrinkable nonwoven fabric comprises self-crimping fiber, the extensibility and contractibility of the nonwoven fabric after shrinkage is preferably such that the recovery from 50% extension after shrinkage by applying hot air at 130° C. flowing at a speed of 1.5 m/sec for 30 seconds is 60% or more, particularly 70 to 95%, for developing sufficiently high elastomeric behavior. The recovery from extension sometimes varies according to the direction of measurement. Sufficient elastomeric behavior will be exhibited as long as the recovery from extension falls within the above range in at least one of the MD and the CD of the nonwoven fabric.

The recovery from extension is measured as follows. Measurement is made with a tensile/compression tester Tensilon RTA-100 supplied by Orientec in the tensile mode. A 50 mm by 50 mm specimen cut out of a shrunken nonwoven fabric that has been heat shrunk under the above-mentioned condition is set between air chucks of the tester at an initial chuck distance of 30 mm. The chuck attached to the load cell (rated output: 5 kg) is moved upward at a pulling speed of 100 mm/min. When the specimen is 50% extended (by 15 mm), the chuck is moved downward to the original position at a speed of 100 mm/min. The readings of the load cell and the extension of the specimen are plotted. The extension recovery is obtained from the plots according to equation:

Extension recovery (%)=[distance of recovery (mm)/maximum extension (=15 mm)]×100 wherein "distance of recovery" is the distance the chuck travels during unloading until the load cell reading reaches zero.

The heat shrinkable nonwoven fabric shrinks on heating at a predetermined temperature. On shrinking, the nonwoven fabric becomes somewhat wavy, which depends on the pattern of fusion bonding. Since shrinkage generally starts at or below the melting point of the constituent resin(s), it is possible to cause the nonwoven fabric to shrink without undergoing deterioration of texture by properly controlling the heat treating conditions.

Figure 7:
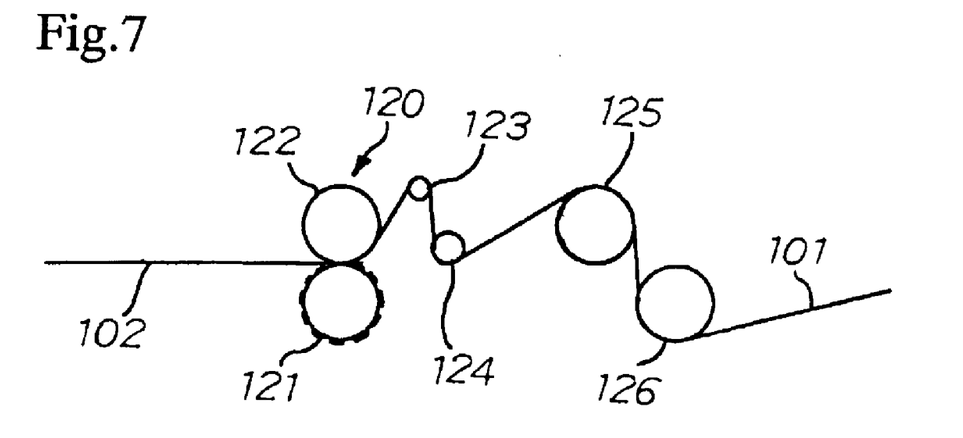
FIG. 7 is a schematic illustration of an apparatus for producing heat shrinkable nonwoven fabric which is preferably used in the production of the topsheet according to the present invention.
Figure 8:
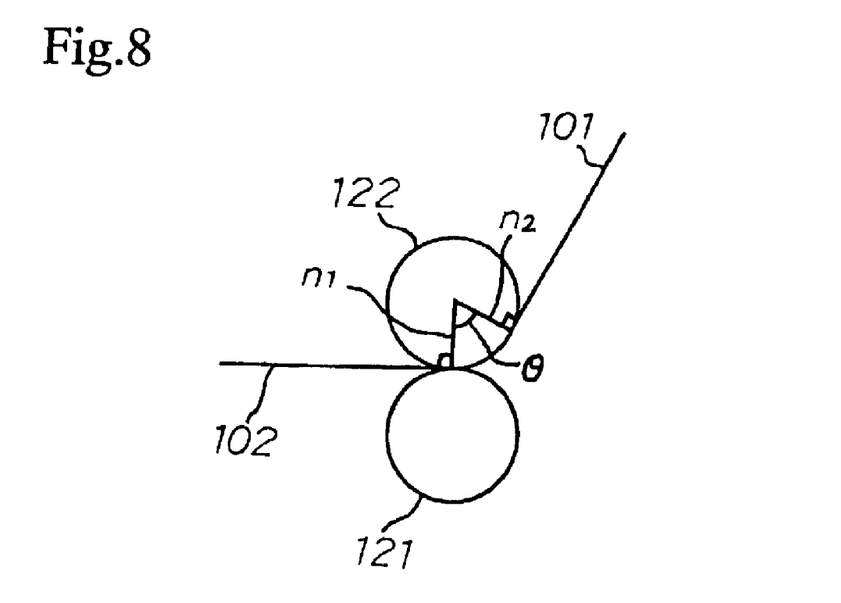
FIG. 8 schematically illustrates the measurement of a wrap angle.

A preferred process for producing the heat shrinkable nonwoven fabric will be described with reference to FIGS. 7 and 8. FIG. 7 shows a preferred apparatus which can be used to produce a heat shrinkable nonwoven fabric 101. First of all, a web 102 containing heat shrinkable fiber is prepared. The process for making the web 102 depends on whether the constituent fiber is short or long. In using short fiber, the web is prepared by entangling short fibers by means of a card. In using long fiber, filaments spun from a spinneret are built up directly on a wire mesh.

The web 102 is passed through a heat embossing machine 120 having two rolls 121 and 122, where heat and pressure are applied to parts of the web 102 to fusion bond the constituent fibers of the parts while the web 102 is under tension. As stated supra, the fusion bonding temperature is equal to or higher than the shrinkage starting temperature $T_s$ of the heat shrinkable fiber. The pressure to be applied is decided appropriately according to the constituent resin of the nonwoven fabric. For example, the pressure to be applied to nonwoven fabric comprising polyethylene terephthalate (PET) is preferably 20 to 50 kgf/cm in terms of linear pressure. The pressure for nonwoven fabric comprising polypropylene is preferably 20 to 120 kgf/cm. The heat embossing machine 120 may have a pair of engraved rolls or a combination of an engraved roll and a smooth roll. Where an engraved roll and a smooth roll are combined, it is preferred for suppressing shrinkage of the heat shrinkable fiber to set the temperature of the engraved roll at or above the shrinkage starting temperature $T_s$ of the heat shrinkable fiber (e.g., $T_s+20°$ C.) and the temperature of the smooth roll below the $T_s$ (e.g., $T_s-5°$ C.). To ensure suppression of thermal shrinkage of the heat shrinkable fiber, it is also preferred to wrap the web around the smooth roll thereby to minimize the contact of the web with the projections of the engraved roll.

Since partial fusion bonding of the web is executed at or above the shrinkage starting temperature of the heat shrinkable fiber, there is a fear of the heat shrinkable fiber's shrinking during the fusion bonding. In the preferred process, this can be avoided by passing the web through the heat embossing machine while applying tension to the web and continuing applying tension to the web which has passed through the embossing machine and is being carried until the temperature of the heat shrinkable fiber of the web reduces lower than its shrinkage starting temperature. By this manipulation, the heat shrinkable fiber is suppressed from shrinking and thereby maintains heat shrinkability after being formed into nonwoven fabric 101. Giving tension also prevents the web from clinging to the rolls and protects the web against excessive heat other than the heat for fusion bonding. The tension is preferably applied in at least one of the MD and the CD of the web. It is particularly preferred to apply tension in both the MD and the CD for effectively preventing the heat shrinkable fiber from shrinking.

Tension in the MD can be applied by, for example, providing a pair of tension rolls 123 and 124 in the downstream of the embossing machine 120, the tension rolls 123 and 124 rotating at higher speeds than the rolls of the embossing machine 120. In order to generate large tension, the tension rolls 123 and 124 are preferably arranged so that the web may pass in an S-shape, wrapping the tension rolls. Tension in the CD can be applied by wrapping the web around the smooth roll 122 at a large wrap angle. The wrap angle around the smooth roll is preferably 30° or larger, still preferably 60 to 90°. As shown in FIG. 8, the wrap angle θ is defined to be an angle formed between the normal n1 to the point of first contact of the web 102 with the smooth roll 122 and the normal n2 to the point where the web 102 separates from the smooth roll 122. The tension to be applied is such that the heat shrinkable fiber may not substantially shrink. Specifically, the MD tension is preferably about 4 to 20 cN/mm for suppressing shrinkage in the MD while controlling crosswise shrinkage, and the CD tension is preferably about 1 to 20 cN/mm for suppressing crosswise shrinkage.

It is preferred to provide the depressions of the engraved roll 121 with a heat insulating material. In this case, the heat shrinkable fiber hardly shrinks even under low tension, and the web's own repulsive force against shrinkage is made use of for applying tension. Useful heat insulating materials include a nylon sheet, a bakelite sheet, an inorganic laminate having a glass fiber base (e.g., Miolex® ), silicone rubber or sponge, and fluorine rubber or sponge. Preferred of them are those having high heat resistance and low thermal conductivity, for example, those having a thermal conductivity of not more than 2 W/mK, particularly 0.1 W/mk or less, which keep their surface temperature lower than the projections by 10 to 20° C., thereby to effectively suppress the heat shrinkable fiber from shrinking. The heat insulating material preferably has a thickness of about 1 to 3 mm for exerting the above-described performance.

Application of tension is continued after the web 102 has passed through the embossing machine 120 until the temperature of the heat shrinkable fiber drops below its shrinkage starting temperature $T_s$. In detail, the MD tension is continued being applied by keeping the rotational speed of the tension rolls 123 and 124 higher than that of the rolls of the embossing machine 120. The CD tension is continued being applied by wrapping the web (which has been formed into nonwoven fabric) around the tension rolls 123 and 124 at large wrap angles to make the web less prone to slide thereby making use of the web's own repulsive force against shrinkage to create tension. The suppressive effect of the tension rolls 123 and 124 on shrinkage can be enhanced by making the surface of the tension rolls of such a material as to produce a large frictional force against the web. The shrinkage-suppressive effect can further be enhanced by using two or more tension rolls. The shrinkage-suppressive effect can furthermore be enhanced by cooling the tension rolls 123 and 124 to accelerate cooling of the web 102. Instead of cooling the tension rolls 123 and 124, it is also effective to provide cooling rolls 125 and 126, around which the web is wrapped, in the downstream of the tension rolls 123 and 124 as shown in FIG. 7. CD tension can also be applied by use of a tenter used in the production of stretched films, such as a pin tenter or a clip tenter.

Once the temperature of the heat shrinkable fiber is reduced lower than its shrinkage starting temperature, shrinkage does not occur with no tension applied. There is thus obtained a heat shrinkable nonwoven fabric 101. The embossing machine composed of rolls used in the above-mentioned process is suited to produce nonwoven fabric of continuous length. A plate type embossing machine can be used in place of the roll type one in the production of cut sheets of nonwoven fabric.

If necessary, the resulting shrinkable nonwoven fabric can be subjected to a post treatment according to the final use, such as ultrasonic bonding, embossing at temperatures lower than the shrinkage starting temperature, or perforating.

The topsheet for absorbent articles according to the present invention is suitable as a topsheet of absorbent articles comprising a liquid permeable topsheet, a liquid impermeable backsheet, and an absorbent member interposed between the topsheet and the backsheet. Such absorbent articles include sanitary napkins, disposable diapers, incontinence pads, and panty liners.

The present invention will now be illustrated in greater detail with reference to Examples, but it should be understood that the invention is not construed as being limited thereto.

EXAMPLE 1

(1) Preparation of First Fiber Layer-Forming Material

Heat bondable core-sheath conjugate fiber consisting of a polyethylene terephthalate core and a polyethylene sheath at a core/sheath weight ratio of 5/5 and having a fineness of 2.2 dtex and a fiber length of 51 mm (NBF-SH, available from Daiwabo Co., Ltd.; hereinafter referred to as non-shrinkable fiber A) was carded into a web and heat treated at 120° C. to prepare a nonwoven fabric having a basis weight of 15 g/m².

(2) Preparation of Second Fiber Layer-Forming Material

Self-crimping fiber which was heat shrinkable core-sheath conjugate fiber consisting of an ethylene-propylene random copolymer (EP) core and a polypropylene ](PP) sheath and having a fineness of 2.2 dtex and a shrinkage starting temperature $T_s$ of 90° C. (available from Daiwabo Co., Ltd.; hereinafter referred to as shrinkable fiber B) was carded into a web. The web was embossed through a heat embossing machine composed of an engraved roll and a smooth roll (embossing roll surface temperature: 145° C.). The shrinkage of the web was suppressed by applying MD tension to the web until the temperature of self-crimping conjugate fiber in the web becomes lower than the heat shrinkage starting temperature $T_s$ of the self-crimping conjugate fiber.

The engraved roll in this embossing had a dot emboss pattern shown in FIG. 4(a), in which the dots (projections) each had a circular shape having an emboss area of 0.0055 cm² and were arrayed at a pitch of 1.4 mm (P1 and P2) in both the MD and the CD to provide a total emboss area ratio of 28%. The resulting heat-embossed nonwoven fabric had a basis weight of 20 g/m².

(3) Preparation of Topsheet

The nonwoven fabrics prepared in (1) and (2) above were superposed on each other and passed through a heat embossing machine composed of an engraved roll and a smooth roll to join them. The engraved roll temperature was set at 155° C. The engraved roll had projections each having a circular shape with an emboss area of 0.047 cm² arrayed at a pitch of 7 mm (P1 and P2) in both the MD and the CD and a pitch of 5 mm (P3) in the direction forming 45° with the MD and the CD to totally make the pattern of FIG. 4(b). The total emboss area ratio was 7.2%.

The four sides of the resulting laminate of the two nonwoven fabrics were fixed on the pins of a pin tenter adjusted to the area to which the laminate was to shrink so that the laminate might not overshrink (shrink more than designed). The laminate as caught on the pin tenter was heat treated in a dryer set at 130° C. for 1 to 3 minutes to obtain a topsheet having a basis weight of 60 g/m².

EXAMPLE 2

Non-shrinkable fiber A and shrinkable fiber B were mixed at an A:B weight ratio of 85:15. The mixed fiber was carded into a web, which was heat treated at 120° C. to prepare a nonwoven fabric having a basis weight of 15 g/m² as a first fiber layer-forming material. A topsheet was produced in the same manner as in Example 1, except for using the resulting first fiber layer-forming material.

EXAMPLE 3

Non-shrinkable fiber A and shrinkable fiber B were mixed at an A:B weight ratio of 70:30. The mixed fiber was carded into a web, which was heat treated at 120° C. to prepare a nonwoven fabric having a basis weight of 15 g/m² as a first fiber layer-forming material. A topsheet was produced in the same manner as in Example 1, except for using the resulting first fiber layer-forming material.

COMPARATIVE EXAMPLE 1

Shrinkable fiber B was carded into a web having a basis weight of 35 g/m². A topsheet was produced in the same manner as in Example 1, except for using the resulting non-embossed web as a second fiber layer-forming material.

COMPARATIVE EXAMPLE 2

A topsheet was produced in the same manner as in Example 1, except for using a spunbond nonwoven fabric made solely of polypropylene fiber and having a basis weight of 12 g/m² as a first fiber layer-forming material.

COMPARATIVE EXAMPLE 3

The nonwoven fabric used as a topsheet in a commercially available sanitary napkin, Laurier Sarasara Cushion Slim (with no wings) supplied from Kao Corp. (hereinafter referred to its sale name "Laurier UN-f-11"), was tested. This topsheet comprises a core-sheath conjugate fiber consisting of a polyethylene terephthalate core and a polyethylene sheath at a core/sheath weight ratio of 5/5 and having a fineness of 2.2 dtex and a fiber length of 51 mm which was made into nonwoven fabric by an air-through process.

COMPARATIVE EXAMPLE 4

The perforated film used as a topsheet in a commercially available sanitary napkin, Laurier Dry-up Mesh Regular (sale name: Laurier DR-h-114) supplied from Kao Corp., was tested. This topsheet comprises a perforated resin film of polyethylene.

The topsheets prepared in Examples and Comparative Examples were examined for basis weight, apparent thickness $t1$ and fiber density $d1$ of the first fiber layer, apparent thickness $t2$ and fiber density $d2$ of the second fiber layer, through-thickness deformation per 1 gf/cm² when compressed under a load of 10 gf/cm², surface whiteness $L1$, and red plate hiding ratio. The results obtained are shown in Table 1.

The performance properties of the topsheet as used in a sanitary napkin (absorbent article) were evaluated as follows.

(a) Preparation of Sanitary Napkin

Sanitary napkins having the same structure as Laurier UN-f- 11 (Kao Corp.) were produced as follows. The topsheet prepared above and a polyethylene film as a backsheet (the one used in Laurier UN-f-11) were set on the upper and the lower sides, respectively, of an absorbent member (the one used in Laurier UN-f-11; thickness: 4.5 mm; an aggregate made of 200 g/m² of fluff pulp and 40 g/m² of an acrylic acid-sodium acrylate copolymer as an absorbent polymer and wrapped in absorbent paper having a basis weight of 16 g/m²). A leak preventive groove and a peripheral seal were formed to make a sanitary napkin.

(b) Surface Whiteness La of Absorbent Article Before Absorption

The surface whiteness La of the absorbent article (sanitary napkin) before absorption was measured with a color difference meter SZ-Σ80 supplied by Nippon Denshoku Industries, Co., Ltd. in the same manner as for the surface whiteness $L1$ of the topsheet, except that the sanitary napkin was placed on the glass mount with the topsheet side facing the light source.

(c) Surface Whiteness Lb of Absorbent Article After Absorption

Simulated blood is prepared as follows. In a 2 liter beaker is put 1500 g of ion-exchanged water, and 5.3 g of sodium carboxymethyl cellulose (CMC-Na, available from Kanto Kagaku K.K.) is dissolved therein by stirring with a magnetic stirrer. Separately, 556 g of ion-exchanged water is put into a 1 liter beaker, and 27.0 g of sodium chloride and 12 g of sodium hydrogencarbonate ($NaHCO_2$, available from Kanto Kagaku) are dissolved therein by stirring with a stirrer. The resulting two solutions and 900 g of glycerin are mixed up by stirring in a 3 liter beaker.

To the mixture are added 15 ml of aqueous solution of nonionic surfactant "Emulgen 935" (available from Kao Corp.) having a concentration of 1 g/L (surfactant/water) and 0.3 g of Red #2 (produced by Daiwa Kasei K.K. and available from Aisen K.K. and Hodogaya Chemical Co., Ltd.), followed by stirring. The mixture is filtered by suction through a glass filter to prepare simulated blood.

Simulated blood may also be prepared by using other nonionic surfactants than the aforementioned one to obtain the same results. However, the amount of surfactant should be adjusted such that the contact angle of the simulated blood falls within the range of 35–40° with respect to the surface of a glass plate. The contact angle is obtained by measuring a contact angle of simulated blood with respect to the glass surface (cleansed by ethanol) with use of a contact angle measuring apparatus (manufactured by KYOWA INTERFACE SCIENCE CO., LTD., FACE Contact Angle Meter CA-A type).

Six grams of the simulated blood put in a 10 ml beaker is carefully poured through a pouring tool on the topsheet side of an absorbent article the surface whiteness of which has been measured. The pouring tool consists of an acrylic plate (100 mm×200 mm×8 mm (t)) having a through-hole of 10 mm in diameter at the center thereof and a hollow cylinder made of a smaller-diametered cylinder of 10 mm in inner diameter and a larger-diametered cylinder of 22 mm in inner diameter concentrically connected in series via a joint tapered at an angle of 45° with the axis of the cylinders, the end of the smaller-diametered cylinder being concentrically joined to the through-hole of the acrylic plate. The pouring tool is placed on the absorbent article with its through-hole at the center of the length and width of the absorbent article. Simulated blood (6 g) is poured into the opening of the larger-diametered cylinder over about 5 seconds and discharged from the hole of the plate. After the pouring, the absorbent article is allowed to stand for 120 seconds, and the surface whiteness Lb is measured in the same manner as for the La value (L value before absorption).

A difference between La and Lb (La–Lb) was obtained. The measured La and Lb values and the different (La–Lb) are shown in Table 1.

Lb (surface whiteness after absorption) is a parameter of the properties of making absorbed menstrual blood less noticeable, which are of particular concern as to the central portion of an absorbent article facing the vaginal opening of a wearer. A higher Lb value means less liquid remaining in the surface layer of the topsheet. An Lb value of 60 or higher assures equality to conventional film type topsheets in color hiding performance, i.e., a clean impression.

A smaller difference between La (L value before absorption) and Lb (L value after absorption) indicates that the liquid is less prone to remain in the surface layer to give a cleaner impression and less causative of overhydration or a skin rash. (La–Lb) values of 40 or greater shows that the liquid oozes out appreciably and remains in the surface layer.

(d) Amount of Liquid Remaining

The amount of liquid remaining in the topsheet was measured as follows to evaluate liquid migration from the topsheet to the absorbent member. A smaller amount indicates smoother migration of liquid to the absorbent member.

A sanitary garment (Laurier Shorts, Standard L size, available from Kao Corp.) having a sanitary napkin stuck to the crotch portion thereof was put on a movable female body model supplied by Takaken K.K. The topsheet used in the sanitary napkin, which had a cut size of 80 mm by 100 mm, had previously been weighed. After the model was operated to take a walking movement of 100 steps/min for 1 minute, 2 g of defibrinated horse blood (available from Nippon Biotest Lab.) was poured into the napkin at a rate of 0.13 g/sec, and the model was operated to take the same walking movement for an additional 29 minute period. After the test, the topsheet was weighed again. The weight gain of the topsheet is the amount of the liquid remaining in the topsheet. The test was conducted three times to obtain an average value. The results obtained are shown in Table 1.

(e) Resistance to Bunching and Wrinkling

Each of the topsheets of Examples and Comparative Examples cut to a size of 75 mm wide and 180 mm long was superposed on Laurier UN-f-11 (Kao Corp.) from which the topsheet had been removed and stapled to the napkin 5 mm wide of each side edge of the absorbent member to the inside at three positions; the front, middle, and rear (6 positions in all).

The thus prepared sanitary napkin was stuck to a sanitary garment (Laurier Standard Shorts, available from Kao Corp.), and the garment was put on the same movable female body model as used in (d) above. The model was operated to take a walking movement. One minute later, 6 g of colored water was poured into the sanitary napkin at a rate of 2 g/15 sec, and the model was continued being operated in a walking mode for 30 minutes. The napkin was removed, and its surface condition was rated by seven female testers in degree of bunching and wrinkling according to the following standard. The results are shown in Table 1.

Standard of Evaluation:

A: Neither bunched nor wrinkled.
B: Bunched and wrinkled to an acceptable degree.
C: Remarkably Bunched and wrinkled.

TABLE 1

| | Example | | | Comparative Example | | | |
|---|---|---|---|---|---|---|---|
| | 1 | 2 | 3 | 1 | 2 | 3 | 4 |
| Sheet-forming Material (before shrinkage) | | | | | | | |
| First Fiber Layer-forming Material: | | | | | | | |
| Basis Weight (g/m$^2$) | 15 | 15 | 15 | 15 | 12 | 25 | 25 |
| Non-shrinkable Fiber (%) | 100 | 85 | 70 | 100 | 100 | 100 | — |
| Shrinkable Fiber (%) | 0 | 15 | 30 | 0 | 0 | 0 | — |
| Second Fiber Layer-forming Material: | | | | | | | |
| Basis Weight (g/m$^2$) | 20 | 20 | 20 | 35 | 25 | — | — |
| Emboss Area Ratio (%) | 28 | 28 | 28 | 0 | 0 | — | — |
| Joint Area Ratio (%) | 7.2 | 7.2 | 7.2 | 7.2 | 7.2 | — | — |
| Topsheet | | | | | | | |
| First Fiber Layer: | | | | | | | |
| Apparent Thickness (mm) | 1.9 | 1.9 | 1.9 | 2.00 | 0.15 | 0.42 | 0.57 |
| Fiber Density d1 (g/cm$^3$) | 0.016 | 0.016 | 0.016 | 0.017 | 0.080 | 0.060 | — |
| Second Fiber Layer: | | | | | | | |
| Apparent Thickness (mm) | 0.45 | 0.45 | 0.5 | 1.00 | 1.18 | — | — |
| Fiber Density d2 (g/cm$^3$) | 0.090 | 0.090 | 0.085 | 0.080 | 0.048 | — | — |
| Density Ratio d2/d1 | 5.63 | 5.63 | 5.31 | 4.71 | — | — | — |
| Total Basis Weight (g/m$^2$) | 60 | 62 | 70 | 100 | 140 | 25 | 27 |
| Percent Area Shrinkage (%) | 50 | 50 | 53 | 56 | 56 | — | — |
| Through-thickness Deformation at 10 gf/cm$^2$ Load (mm/gf/cm$^2$) | 0.08 | 0.08 | 0.09 | 0.08 | 0.16 | 0.05 | 0.01 |
| Whiteness L1 | 65 | 66 | 65 | 80 | 60 | 62 | 75 |
| Red Plate Hiding Ratio (%) | 42 | 43 | 43 | 65 | 40 | 34 | 56 |
| Absorbent Article | | | | | | | |
| Surface Whiteness before Absorption La | 94 | 95 | 95 | 96 | 96 | 96 | 97 |
| Surface Whiteness after Absorption Lb | 76 | 74 | 75 | 74 | 54 | 60 | 74 |
| La – Lb | 18 | 21 | 20 | 22 | 42 | 36 | 23 |
| Amount of Remaining Liquid (mg) | 45 | 43 | 42 | 100 | 140 | 40 | 0.1 |
| Resistance to Bunching | A | 6 | — | — | 4 | 2 | 1 | 2 |

TABLE 1-continued

|  |  | Example | | | Comparative Example | | | |
| --- | --- | --- | --- | --- | --- | --- | --- | --- |
|  |  | 1 | 2 | 3 | 1 | 2 | 3 | 4 |
| or Wrinkling (Number of Testers) | B | 1 | — | — | 3 | 5 | 1 | 0 |
|  | C | 0 | — | — | 0 | 0 | 5 | 5 |

The process for producing the heat shrinkable nonwoven fabric which is preferably used in the process of producing the topsheet for absorbent articles according to the present invention as a second fiber layer-forming material having densified parts will further be described.

PREPARATION EXAMPLE 1

Figure 9:
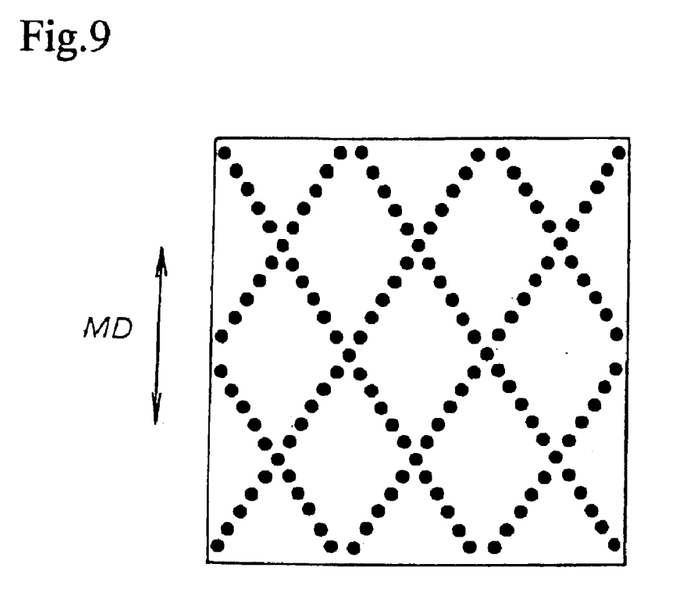
FIG. 9 shows an emboss pattern of an engraved roll.

Self-crimping fiber which was core-sheath conjugate fiber consisting of an ethylene-propylene random copolymer (EP) core and a polypropylene (PP) sheath and having a shrinkage starting temperature $T_s$ of 90° C. (available from Daiwabo Co., Ltd.) was carded into a web, the basis weight of which is shown in Table 2 below. The web was heat embossed through a heat embossing machine composed of an engraved roll and a smooth roll at a processing speed shown in Table 1. Other heat embossing conditions are shown in Table 2. The wrap angle of the web around the smooth roll was 0°. The emboss pattern of the engraved roll was as shown in FIG. 9. An MD tension was applied to the web when the web passed through the heat embossing machine and thereafter until the temperature of the self-crimping fiber of the web reduced below the shrinkage starting temperature $T_s$ of the self-crimping fiber. The MD tension was applied by means of a pair of tension rolls provided in the downstream of the embossing machine. The rotational speed of the tension rolls were set higher than that of the rolls of the embossing machine. The basis weight of the resulting embossed nonwoven fabric is shown in Table 2.

PREPARATION EXAMPLE 2

A heat embossed nonwoven fabric was obtained in the same manner as in Preparation Example 1, except for wrapping the web around the smooth roll at a wrap angle of 60° and changing the other heat embossing conditions as shown in Table 2. The basis weight of the resulting nonwoven fabric is shown in Table 2

REFERENCE EXAMPLE 1

The same self-crimping fiber as used in Preparation Example 1 was carded into a web, the basis weight of which is shown in Table 2. The web was needled with a water stream at a processing speed shown in Table 2 to prepare a spunlace nonwoven fabric.

REFERENCE EXAMPLE 2

The same self-crimping fiber as used in Preparation Example 1 was carded into a web, the basis weight of which is shown in Table 2.
Evaluation:
(i) The MD tensile strength of the nonwoven fabrics and the web prepared in Preparation Examples and Reference Examples was measured. The percent shrinkage of these samples was measured as follows. The MD and CD extension recovery from 50% extension of shrunken nonwoven fabrics and the web was measured. The results obtained are shown in Table 2.
Measurement of Percent Shrinkage:
The nonwoven fabric or web was allowed to shrink by applying hot air at 130° C. flowing at a speed of 1.5 m/sec for 30 seconds. The percent shrinkage was calculated from the areas before and after the shrinkage according to equation: (area before shrinkage−area after shrinkage)/area before shrinkage×100. The aforementioned extension recovery was measured with respect to the shrunken nonwoven fabrics and the web thus obtained.

TABLE 2

|  |  | Preparation Example | | Reference Example | |
| --- | --- | --- | --- | --- | --- |
|  |  | 1 | 2 | 1 | 2 |
| Web | Material | self-crimping fiber ($T_s$: 90° C.) | | | |
|  | Basis Weight (g/m²) | 25 | 20 | 50 | 25 |
| Web Processing | Processing Speed (m/min) | 80 | 80 | 20 | — |
|  | Process | heat embossing | heat embossing | spunlacing | none |
| Conditions | Engraved Roll Temp. (° C.) | 145 | 155 | — | — |
|  | Smooth Roll Temp. (° C.) | 150 | 155 | — | — |
|  | Heat Insulator on Engraved Roll | none | none | — | — |
|  | MD Tension (cN/mm) | 6 | 6 | — | — |
|  | Wrap Angle around Smooth Roll (°) | 0 | 60 | — | — |
|  | Emboss Area Ratio (%) | 28 | 18 | — | — |
| Nonwoven Fabric | Basis Weight (g/m²) | 25 | 20 | 50 | 25 (as web) |
|  | MD Tensile Strength (gf/50 mm) | 1290 | 703 | 1300 | 100 or lower |
|  | Percent Shrinkage (%) | 88 | 70 | 81 | 88 |

TABLE 2-continued

|  |  | Preparation Example | | Reference Example | |
| --- | --- | --- | --- | --- | --- |
|  |  | 1 | 2 | 1 | 2 |
| Extension Recovery | MD | 85 | 93 | 80 | 94 |
| (%) | CD | 77 | 87 | 70 | 87 |

As is apparent from the results shown in Table 2, the thermal bond nonwoven fabrics prepared in Preparation Examples exhibited high shrinkability and developed high extensibility and contractibility after shrinkage. It is also seen that the heat embossed nonwoven fabrics of Preparation Examples showed substantially no change in basis weight from the starting webs, which reveals that the heat shrinkable fiber had underwent no shrinkage on heat embossing. The spunlace nonwoven fabric of Reference Example 1 also showed high shrinkability and developed extensibility and contractibility after shrinkage, but the processing speed was low, i.e., the productivity was low. The carded web of Reference Example 2 was too weak for practical use.

The heat shrinkable nonwoven fabrics obtained in Preparation Examples have sufficient strength for handling. That is, they are smoothly fed from a stock roll and smoothly conveyed on a carrying unit. They can be produced at a high production speed, which reduces the production cost, with an arbitrary basis weight from small to large. Further, the heat shrinkable nonwoven fabrics have excellent texture even after shrinkage.

Figure 10:
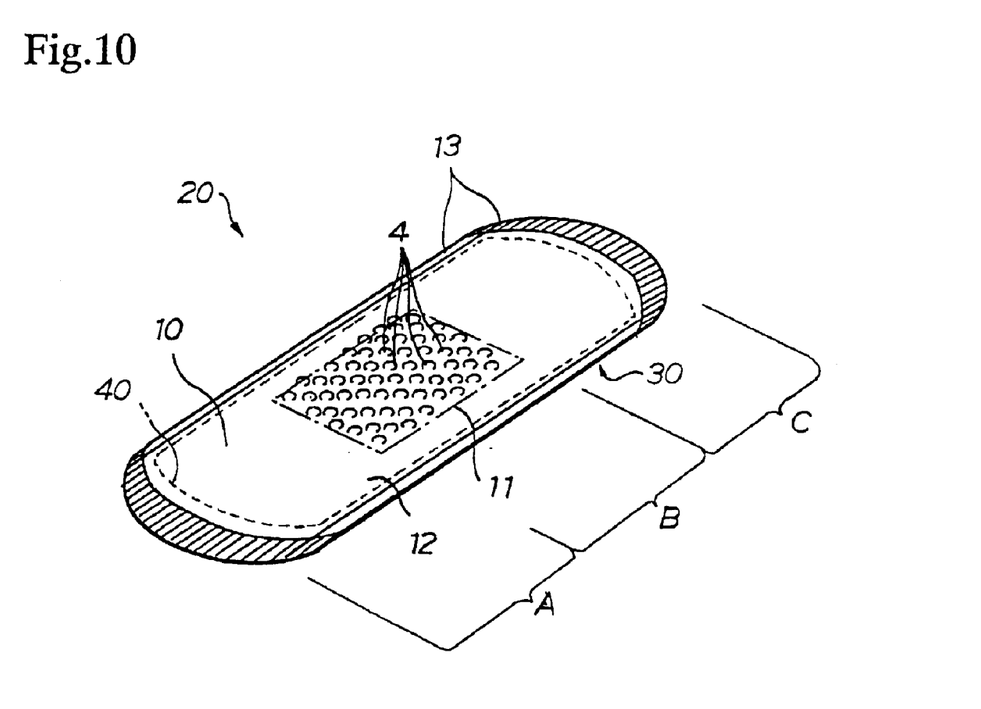
FIG. 10 is a perspective view of a sanitary napkin produced by using the topsheet of the present invention.

The topsheet of the present invention as used in an absorbent article does not always need to have protrusions 4 on the entire surface of its side to be brought into contact with a wearer. For example, the sanitary napkin 20 shown in FIG. 10 comprises a liquid permeable topsheet 10, a liquid impermeable backsheet 30, and a liquid retentive absorbent member 40 interposed between the two sheets, in which the topsheet 10 has an uneven area 11 having a large number of protrusions 4 in a regular pattern and a less uneven area 12 having protrusions much lower than the protrusions 4. The protrusions 4 in the uneven area 11 are those formed by partially joining a first fiber layer-forming material and a second fiber layer-forming material (heat shrinkable nonwoven fabric containing heat shrinkable fiber and having part of its constituent fiber fusion bonded by heat embossing into densified parts), followed by shrinking thereby to raise the first fiber layer-forming material in portions other than the joints between the first fiber layer-forming material and the second fiber layer-forming material. The less uneven area 12 is the area of the joined material where the second fiber layer-forming material has not shrunken sufficiently. The protrusions in the less uneven area 12, being far smaller in height than the protrusions 4 of the uneven area 11, are not shown in the drawing. The sanitary napkin 20 being divided into three portions along its longitudinal direction: the front portion A, the middle portion B the widthwise middle of which is to face the vaginal opening of a wearer, and the rear portion C, the uneven area 11 is disposed in the middle portion B, more specifically in the widthwise middle of the middle portion B which is to be placed on the vaginal opening. The less uneven area 12 is disposed to surround the uneven area 11.

Figure 11A:
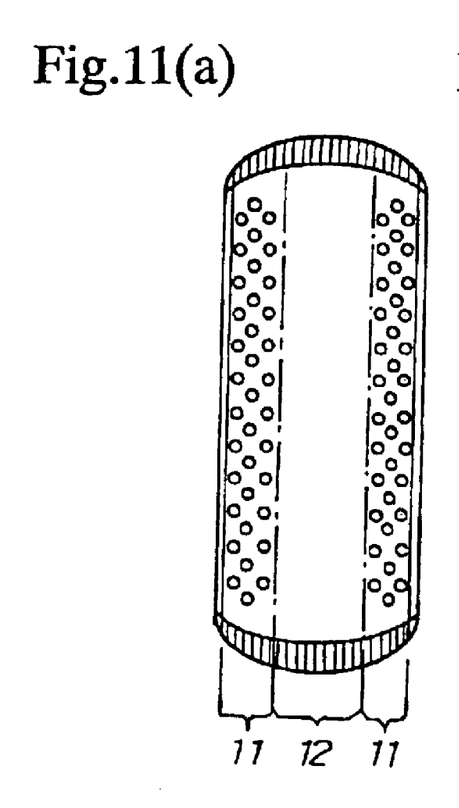
FIGS. 11(a) and 11(b) are each a plan view of another sanitary napkin produced by using the topsheet of the present invention.
Figure 11B:
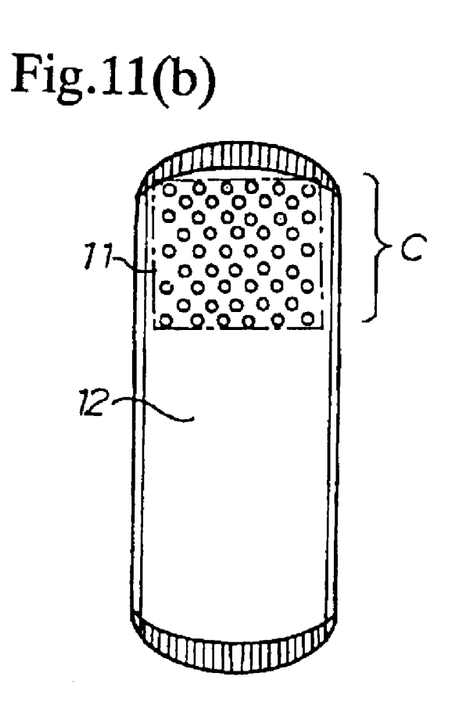

The sanitary napkin shown in FIG. 11(a) has the uneven area 11 on both side portions along the longitudinal direction thereof and the less uneven area 12 between the two uneven areas 11. The sanitary napkin shown in FIG. 11(b) has the uneven area 11 on the rear portion C and the less uneven area 12 on the other portions.

The topsheet of the invention may be used as stuck to only a part of the surface of an absorbent article, e.g., the middle portion, the side portions or the rear portion.

The topsheet of the invention is capable of passing body fluids such as menstrual blood and urine to the underlying absorbent member, has softness, and hardly bunches up or wrinkles.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

This application claims the priority of Japanese Patent Application Nos. 2002-47354 filed Feb. 25, 2002and 2002-82173 filed Mar. 22, 2002, which are incorporated herein by reference.

What is claimed is:

1. A topsheet for an absorbent article comprising a first fiber layer disposed on the side of a wearer and a second fiber layer disposed on the side of an absorbent member, said first fiber layer and said second fiber layer being partially bonded together at joints in a prescribed pattern, said first fiber layer having protrusions on the side of a wearer in portions other than the joints, and said second fiber layer being a fiber aggregate containing a heat shrinkable fiber and having heat shrunken parts that have shrunken and densified parts that have been inhibited from heat shrinkage, and wherein said densified parts are arranged at a smaller pitch than said joints.

2. The topsheet for an absorbent article according to claim 1, wherein said densified parts are formed by heat embossing said fiber aggregate before heat shrinkage.

3. The topsheet for an absorbent article according to claim 1, wherein said second fiber layer contains 30 to 100% by weight of a heat shrinkable fiber, and said first fiber layer contains 50 to 100% by weight of a fiber that does not shrink at the shrinkage starting temperature of the heat shrinkage fiber and further contains a heat shrinkable fiber in a proportion of from 0% by weight up to a percent by weight lower than the content of the heat shrinkable fiber of said second fiber layer.

4. The topsheet for an absorbent article according to claim 1, wherein said first fiber layer has an apparent thickness t1 of 0.1 to 3 mm, said second fiber layer has an apparent thickness t2 of 0.2 to 1.5 mm, and the topsheet has a total basis weight of 20 to 80 g/m$^2$.

5. The topsheet for an absorbent article according to claim 1, wherein the topsheet has at least one densified part per protrusion.

6. The topsheet for an absorbent article according to claim 1, wherein the heat shrinkable fiber is a self-crimping fiber.

* * * * *